United States Patent
Dick et al.

[11] Patent Number: 6,164,818
[45] Date of Patent: Dec. 26, 2000

[54] METHOD AND APPARATUS FOR MEASURING VISCOUS HEATING OF VISCOELASTIC MATERIALS

[75] Inventors: John S. Dick, Akron; Henry Pawlowski, Seville, both of Ohio

[73] Assignee: Alpha Technologies, Akron, Ohio

[21] Appl. No.: 09/234,768

[22] Filed: Jan. 21, 1999

[51] Int. Cl.$^7$ ............................. G01N 3/24; G01N 3/22; G01N 11/10

[52] U.S. Cl. ............................. 374/46; 374/48; 374/49; 374/47; 374/55; 73/54.42; 73/54.43; 73/54.39; 73/846

[58] Field of Search ................ 374/46, 48, 49, 374/55, 187, 47; 73/54.42, 54.43, 54.39, 846

[56] References Cited

U.S. PATENT DOCUMENTS

| | | | |
|---|---|---|---|
| 3,182,494 | 5/1965 | Beatty et al. | 374/48 |
| 3,479,858 | 11/1969 | Umeno et al. | 374/48 |
| 3,554,003 | 1/1971 | Wise | 374/48 |
| 3,583,206 | 6/1971 | Espinal et al. | 374/48 |
| 3,769,830 | 11/1973 | Porter et al. | 374/48 |
| 4,266,424 | 5/1981 | Muenstedt | 374/49 |
| 4,343,190 | 8/1982 | Danco et al. | 73/846 |
| 4,552,025 | 11/1985 | Barker et al. | 73/846 |
| 4,754,645 | 7/1988 | Piche et al. | 73/597 |
| 4,829,830 | 5/1989 | Tosaki | 374/48 |
| 4,878,379 | 11/1989 | Deer | 374/46 |
| 5,079,956 | 1/1992 | Burhin et al. | 374/47 |
| 5,133,210 | 7/1992 | Lesko et al. | 374/46 |
| 5,481,903 | 1/1996 | King et al. | 73/54.28 |
| 5,905,196 | 5/1999 | Parshall | 73/54.31 |
| 6,000,279 | 12/1999 | Watson | 73/54.39 |
| 6,023,952 | 2/2000 | Wang et al. | 73/54.09 |

OTHER PUBLICATIONS

J.Fee et al. "Instrument for Measuring Thermal Elastic Behaviour of Hide and Modified Hide Materials", The Journal of American Leather Chemists Association, vol. LI, No. 10, Oct. 1956.

"Miscellaneous Applications of Viscoelastic Properties," Ferry, John D.; Viscoelastic Properties of Polymers, p. 575.

*Primary Examiner*—G. Bradley Bennett
*Assistant Examiner*—Gail Verbitsky
*Attorney, Agent, or Firm*—Robert H. Earp, III; Raymond A. Miller

[57] ABSTRACT

Method and apparatus for measuring viscous heating/heat build-up of viscoelastic materials, such as rubber and polymer compounds. Temperature changes in the viscoelastic material are measured during application of a shearing force to the viscoelastic material. The shearing force is applied by rotating a second die plate relative to a first die plate, which remains stationary. Temperature changes in the viscoelastic material attributable to friction between the first die and an adjacent sealing ring are accounted for, and subtracted out of the final temperature values. The present invention provides an accurate, quantifiable, and repeatable measure of viscous heating/heat build-up of a viscoelastic material.

20 Claims, 8 Drawing Sheets

METHOD AND APPARATUS FOR MEASURING VISCOUS HEATING OF VISCOELASTIC MATERIALS

FIELD OF INVENTION

The present invention generally relates to an improved method and apparatus for measuring the properties of viscoelastic materials, and more specifically to a method and apparatus for measuring viscous heating of viscoelastic materials.

BACKGROUND OF THE INVENTION

It is frequently necessary to incorporate admixtures (e.g., fillers, reinforcing agents, accelerators and antioxidants) into a viscoelastic material (e.g., rubber or polymer compounds) in order to obtain the desired properties for a particular application. In this regard, various admixtures are mixed into the viscoelastic material in mixers, masticating machines, or on roll mills. These substances may include carbon black (for improved abrasion and wear resistance, tensile strength, tear resistance, modulus and hardness), silica, calcium carbonate, clay, oils (for better workability of the mixture), paraffin (for better resistance to light), antioxidants (e.g., aromatic amines or phenol derivatives), activators (e.g., zinc oxide), and various organic and inorganic coloring substances. Moreover, in order to speed up the vulcanization process and to improve the properties of vulcanizates, various accelerators may be added (e.g., dithiocarbamic acid derivatives, mecapto benzothiazole derivatives, diphenylguanidine, etc.). It should be understood that the term "admixture" as used herein includes additives and compounding ingredients.

When a viscoelastic material is processed (e.g., a mixing or extrusion process) work is put into the material, causing the temperature of the material to rise due to the poor thermoconductivity of the viscoelastic material. This heating process is referred to as "viscous heating." Viscous heating of a viscoelastic material during a mixing or extrusion process can have a significant effect on the properties of the viscoelastic material. In this regard, the elevated temperature of the material causes a decrease in the viscosity of the material. As a result, the material is unable to properly disperse fillers or other admixtures.

Different admixtures (e.g., fillers, reinforcing agents, accelerators and antioxidants) will cause different degrees of viscous heating depending on the type of admixture, its average particle size and distribution, primary and secondary structure, and particle shape. If the viscous heating is too great, a batch of viscoelastic material may rise in temperature too rapidly forcing the batch to be discharged before adequate dispersion is achieved. Consequently, an additional pass in an internal mixer may be required, which increases the total mixing time and cost.

For example, the use of carbon black will impart higher hysteresis and heat buildup to the vulcanizate as well as significantly increasing viscous heating during the mixing and processing of a viscoelastic compound. Accordingly, it would be very useful to be able to measure accurately and study the different degrees of viscous heating imparted by different carbon blacks to a rubber batch. Usually in a rubber mixing operation, a particular compound may require two, three, or more "passes" in a factory internal mixer before an acceptable state of dispersion is achieved. A major limiting factor for the time length of a mixing cycle is determined from viscous heating. If a reinforcing filler such as certain carbon blacks quickly raise the temperature of the batch to very high levels, the viscosity of the batch drops so low at this high temperature that little useful mixing action will take place. Therefore, there becomes a need for multiple passes. It would be useful to be able to compare the viscous heating effects of different admixtures in order to predict the useful mixing time possible per batch.

In the prior art, there are many well known instruments for determining various properties of viscoelastic materials (e.g., rubber and like materials). These instruments include such apparatus commonly referred to as Moving Die Rheometers (MDR), Rubber Process Analyzers (RPA), Oscillating Disk Rheometers (ODR), and Mooney Viscometers. These instruments apply a rotational shear to a sample of viscoelastic material and measure the resulting torque. It should be understood that the applied rotational shear may be oscillatory or continuous. In the case of an MDR or RPA, a sample of viscoelastic material to be tested is enclosed in a cavity formed between two opposing dies, and the rotational shear is applied to the sample by rotating one die, while the other die remains stationary, and the torque required to apply the shear is measured. In the case of an ODR or Mooney Viscometer a sample of viscoelastic material to be tested is enclosed in a cavity formed between two opposing dies, rotational shear is applied to the sample by means of a rotor embedded in the sample, and the torque required to apply the shear is measured. In U.S. Pat. Nos. 3,479,858; 4,343,190; and 4,552,025, the force is applied by rotation of one die relative to the other, and the measurements made are of the torque required to apply the shearing force or of the torque induced in the first die (reaction torque) when the second (driven) die is rotated.

While such existing instruments have been used to measure such items as elastic torque, viscous torque, and complex torque, none of these instruments can measure viscous heating caused by application of a shearing force to the sample material. The present invention provides a method and apparatus for measuring the viscous heating of a viscoelastic material.

SUMMARY OF THE INVENTION

According to the present invention there is provided a method for measuring viscous heating of a viscoelastic material, which includes the steps of applying a predetermined pressure to the viscoelastic material; regulating heating means to bring the viscoelastic material to a first predetermined temperature; applying a shearing force to the viscoelastic material; and measuring the change in temperature of the viscoelastic material during application of the shearing force, to obtain heat values.

In accordance with another aspect of the present invention there is provided an apparatus for measuring viscous heating of a viscoelastic material, comprising: means for applying a predetermined pressure to the viscoelastic material; heating means for heating the viscoelastic material; control means for regulating the heating means to bring the viscoelastic material to a first predetermined temperature; means for applying a shearing force to the viscoelastic material; and means for measuring the change in temperature of the viscoelastic material during application of the shearing force, to obtain heat values.

An advantage of the present invention is the provision of a method and apparatus for measuring viscous heating of a viscoelastic material, wherein accurate, quantifiable and repeatable measurements are obtained.

Still another advantage of the present invention is the provision of a method for measuring viscous heating which can be easily implemented using existing viscoelastic measuring apparatus with relatively minor modification thereto.

Still another advantage of the present invention is the provision of an apparatus for measuring viscous heating which can be easily implemented by relatively minor modification of existing viscoelastic measuring apparatus.

Yet another advantage of the present invention is the provision of an apparatus which is suitable for both curing a viscoelastic material and analyzing viscous heating/heat build-up thereof.

Yet another advantage of the present invention is the provision of an apparatus which is suitable for measuring viscous heating/heat buildup of viscoelastic materials in both the uncured and cured state.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

Figure 1:
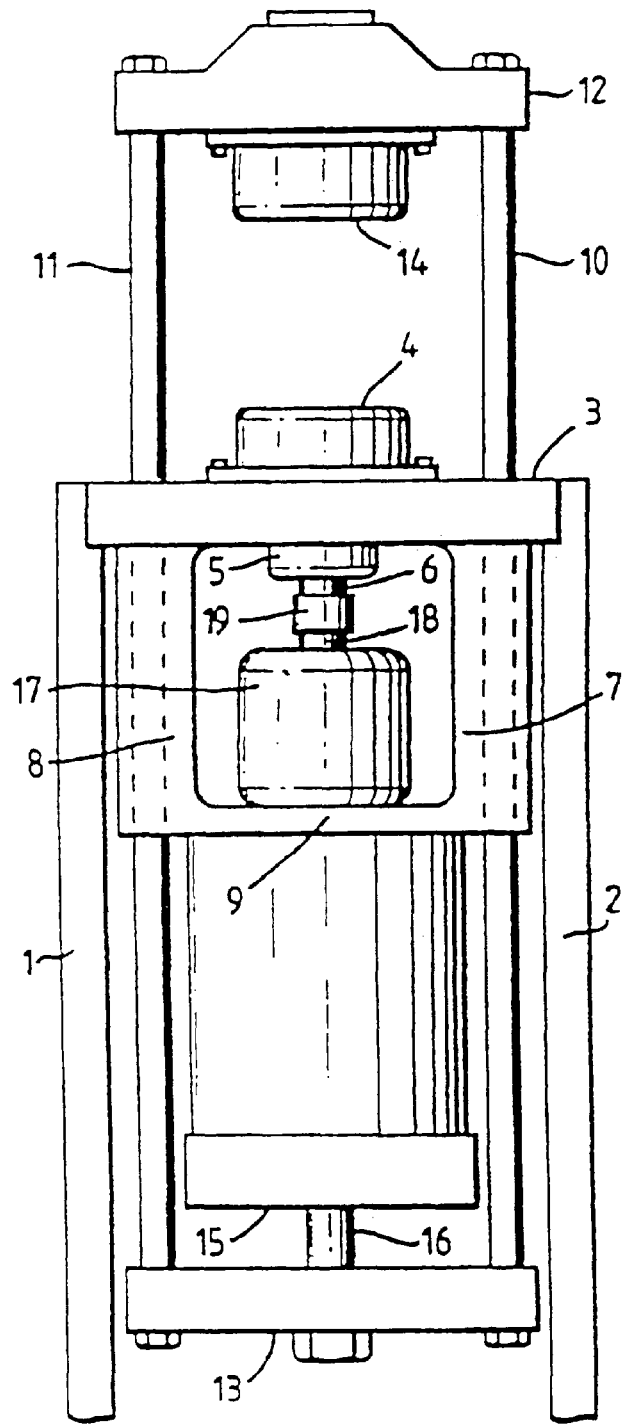
FIG. 1 is a front plan view of an exemplary prior art instrument for measuring the properties of viscoelastic materials.

Referring now to the drawings wherein the showings are for the purposes of illustrating a preferred embodiment of the invention only and not for purposes of limiting same, FIG. 1 illustrates an exemplary instrument for measuring the properties of viscoelastic materials. It will be appreciated that the instrument for measuring the properties of viscoelastic materials may take a variety of other suitable forms, as indicated above (e.g., MDR, RPA, ODR, Mooney Viscometer, etc.). Apparatus A1 includes members 1, 2 and 3, which are respectively left and right vertical and horizontal components of an outer frame which is supported on a base (not shown). A lower (second) die assembly comprising a lower die housing 4 and a housing 5 for a drive shaft 6, is mounted in the horizontal member 3. Drive shaft 6 is connected at its upper end to a lower die (not shown). An inner frame, which is located beneath horizontal member 3 has vertical portions 7 and 8, and a lower horizontal portion 9. Tie rods 10 and 11, which pass through horizontal member 3, are attached at their lower ends to a lower crosshead 13. An upper (first) die assembly, comprising an upper die housing 14, is mounted in an upper crosshead 12. A pneumatic cylinder 15 mounted beneath the horizontal portion 9 of the inner frame has a cylinder rod 16 which is connected to the lower crosshead 13. Actuation of pneumatic cylinder 15 causes the assembly consisting of a cylinder rod 16, lower crosshead 13, tie rods 10, 11 and upper crosshead 12 to travel downwards, thus bringing upper die housing 14, lower die housing 4, and the dies into the closed position. The drive system to the lower die includes a computer controlled electric motor 17, mounted with its output shaft 18 coaxial with drive shaft 6 to the lower die. The two shafts 18, 6 are coupled by means of a sleeve 19.

General operation of apparatus A1 is as follows: The two opposing dies are first moved to an open position, so that a sample of viscoelastic material can be place between the dies. In some cases the sample will be sandwiched between layers of film. It should be appreciated that the sample of viscoelastic material may include one or more admixtures. Next, the two opposing dies are moved to a closed position to form a sealed test cavity, wherein the sample of viscoelastic material is maintained at a predetermined pressure (e.g., 400 psi). The temperature of the dies is controlled during the measurement process. The sample is then subjected to an oscillating (sinusoidal), rotary shear force having a predetermined amplitude and frequency. A torque is measured, which is indicative of the response of the sample material to the shearing force. Information is derived on the properties of the sample material from such measurements. As indicated above, shear force is applied to the sample material by rotation of one die relative to the other. Generally, the shearing force (strain) applied is at least one amplitude of oscillation (i.e., angle), within the range of approximately +/−10° arc to +/−360° arc, and a frequency of oscillation within the range of approximately 0.001 to 33 Hz. The torque measurements are the torque required to apply the shearing force or of the torque induced in the first die (reaction torque) when the second die (driven) is rotated. It will be appreciated that other configurations for apparatus A1 are also suitable for implementing the present invention.

Each die is, in general terms, a circular disc rotatable in a co-axial cylindrical housing surrounding the die. At least one annular seal of heat-resistant elastomeric material is seated in a groove in an axially-extending face of the die or housing and in contact with an adjacent axially-extending face of the housing or die respectively. These seals have been required in order to maintain a relatively constant pressure on the sample during the test.

Figure 2:
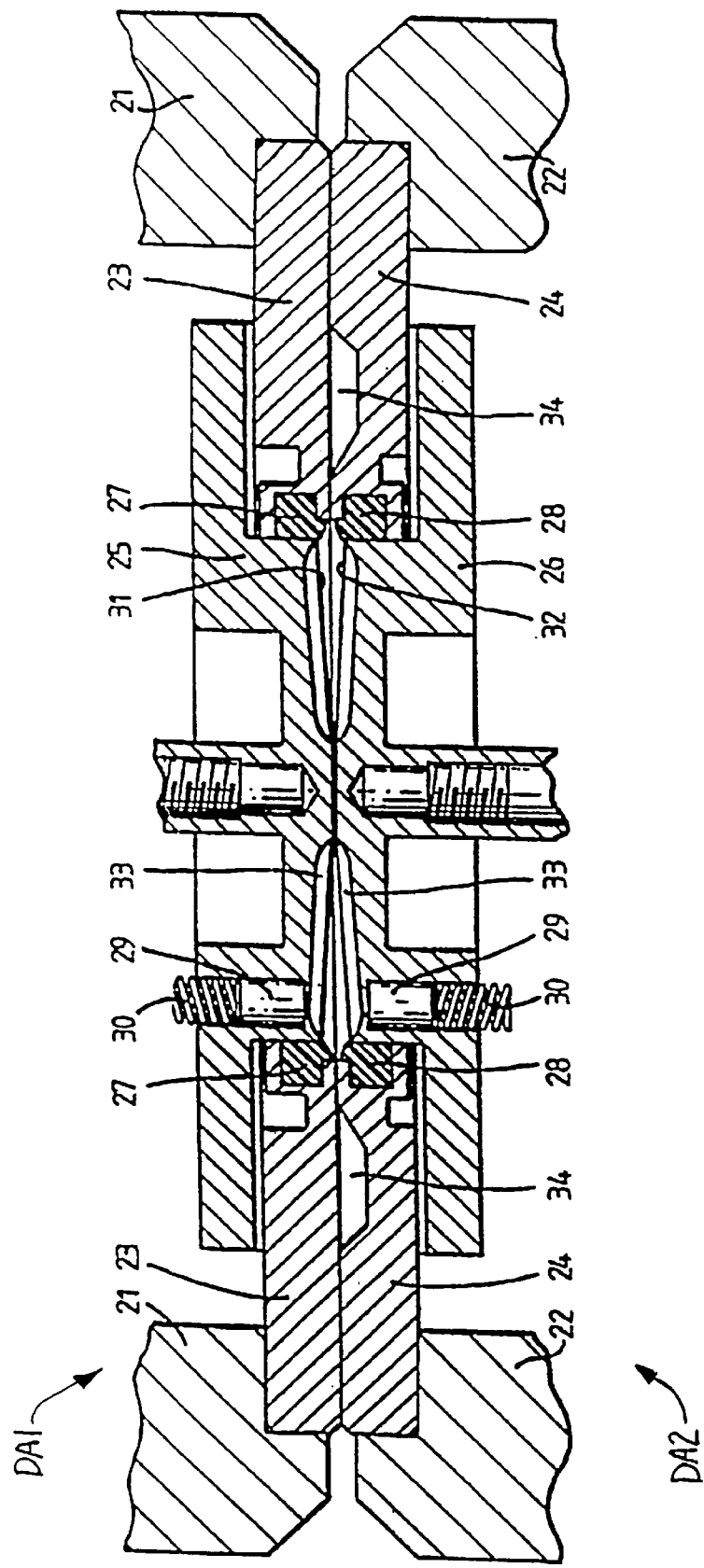
FIG. 2 is a vertical cross-section showing conventional upper and lower die assemblies in the closed position.

FIG. 2 illustrates the parts of the upper and lower die assemblies DA1, DA2, in accordance with a typical apparatus for measuring viscoelastic properties. The lower edge of the upper die housing and the upper edge of the lower die housing are indicated at 21 and 22 respectively. Other parts shown are upper and lower sealing plates 23 and 24, which are attached to the edges of the die housings, stationary upper die plate 25 and rotatable lower die plate 26, and sealing rings 27 and 28. Each die plate 25, 26 has a cylindrical cavity 29 adapted to accommodate a respective temperature probe 30 (e.g., a platinum resistance thermometer). Temperature probes 30 provide an indication of the temperature of the sample material adjacent to the respective die plates. The opposing faces 31 and 32 of die plates 25, 26, which define a die cavity, are in the form of shallow flat-topped cones having radial grooves 33. Thus, a sample in the die cavity has a thin, flat circular portion in the middle, and an outer portion which increases in thickness radially outwards. The function of channels 34 in the lower sealing plate 24 is to accommodate any overflow of the sample material which is expressed during closure of the dies. Channels 34 may also be formed in upper sealing plate 23. It should be noted that there will be a small amount of friction between die plate 26 and sealing ring 28, as die plate 26 oscillates. This friction will generate some measurable heat, as will be explained in detail below.

It will be appreciated that many viscoelastic materials (e.g., rubber) are poor conductors of heat, and thus it is often difficult to measure the temperature at the center of a sample. However, the present invention is particularly well suited to accurate temperature measurements because the upper and lower die plates 25, 26 provide a high surface area in relation to the mass of the sample material, which is compressed very thin. As a result, temperature probes 30 provide accurate temperature measurements of the sample material.

Parts of the upper and lower die assemblies DA1, DA2 which are not illustrated, are generally similar to those shown in FIG. 2 of U.S. Pat. No. 4,552,025 are (in upper die assembly DA1) a torque transducer, means connecting the upper die plate 25 to the force transducer, and a heating element for heating upper die plate 25; and in the lower die assembly DA2, a shaft coaxial with the lower die plate 26, means connecting the lower die plate 26 to the shaft, a bearing housing for the shaft, and a heating element for heating lower die plate 26.

In accordance with the method of the present invention, sample material (e.g., rubber or polymer compound) is subjected to pressure applied by die plates 26. In this regard, die plates 25 and 26 are moved to a closed position, which seals the sample material within a die cavity defined by opposing faces 31 and 32 of die plates 25, 26. As indicated above, the sample of viscoelastic material may include one or more admixtures (e.g., fillers, reinforcing agents, etc.). In the case of evaluating an uncured sample material, the heating elements are activated to heat the sample material to a temperature (Tprelim) which allows the die cavity to be fully closed. In the fully closed position, the sample material will be properly seated between die plates 25, 26 to obtain accurate measurements. Tprelim is a temperature which lowers the viscosity of the sample material to a level wherein the die cavity can be fully closed with the associated apparatus. In most cases, Tprelim will be in the range of approximately 70° to 120° C. However, in some cases Tprelim may be a temperature above 120° C.

Next, the heating elements are deactivated and the sample material is allowed to cool to a predetermined starting temperature (Tstart). It should be noted that both the die plates 23, 26 will be brought to Tstart. Cooling may be facilitated by a cooling device, such as an air blower which blows air on the die plates 25, 26. For evaluating an uncured sample material, Tstart is preferably within the range of approximately room temperature (typically 20°–25° C.) to 120° C. Once the temperature has stabilized (i.e., reached thermal equilibrium) at Tstart, the heating elements and cooling devices are deactivated, and lower die plate 26 begins oscillating at a predetermined amplitude and predetermined frequency. As a result, a shearing force is applied to the sample material. It should be appreciated that the respective heating elements may be regulated to stabilize the temperature at Tstart. While in accordance with a preferred embodiment of the present invention the shearing force is applied by oscillation, the shearing force may alternatively be applied by a continuous rotation. Application of the shearing force causes a change in temperature of the sample material, which is used to obtain heat values.

It should be understood that the respective heating elements may be turned ON and OFF in order to stabilize the temperature of the die plates at Tstart. Moreover, stabilization at Tstart may be established by detecting Tstart for a predetermined period of time (e.g., 60 seconds). It should be further noted that Tstart should not exceed a temperature wherein the viscosity of the sample material reaches such a low level that the amount of viscous heating is no longer measurable.

It should be further appreciated that it may not be necessary to heat the sample material to Tprelim, prior to stabilizing the temperature at Tstart. In this regard, it may be possible, depending upon the configuration of the apparatus and the properties of the sample material, to fully close the die cavity at a temperature equal to or less than Tstart. In this case, the heating element is regulated to ramp up and stabilize the temperature at Tstart.

Figure 3:
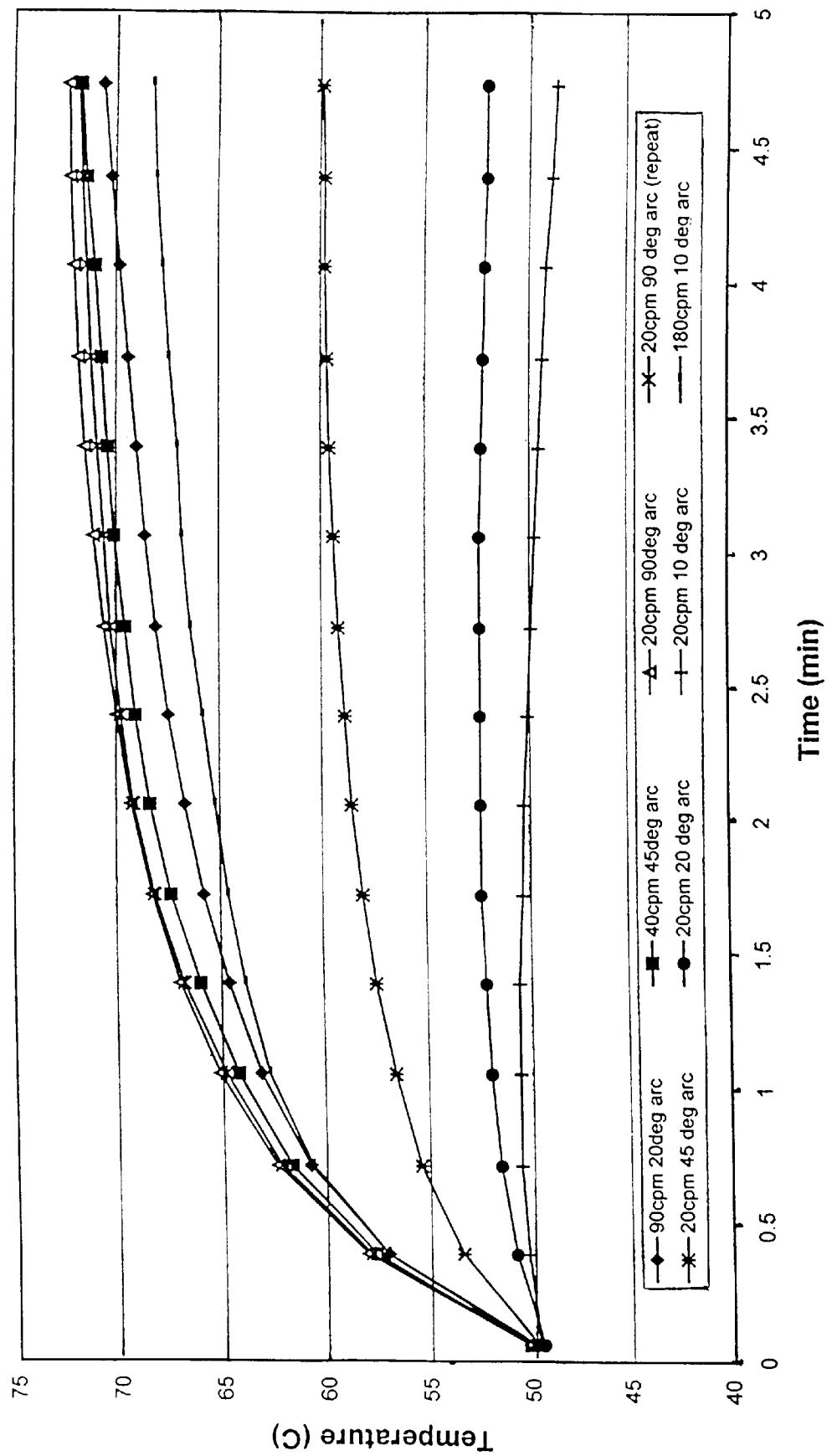
FIG. 3 is a temperature profile of a lower die plate from viscous heating of an SBR compound with 75 phr N351, wherein the die cavity is filled with an elastomeric material.
Figure 4:
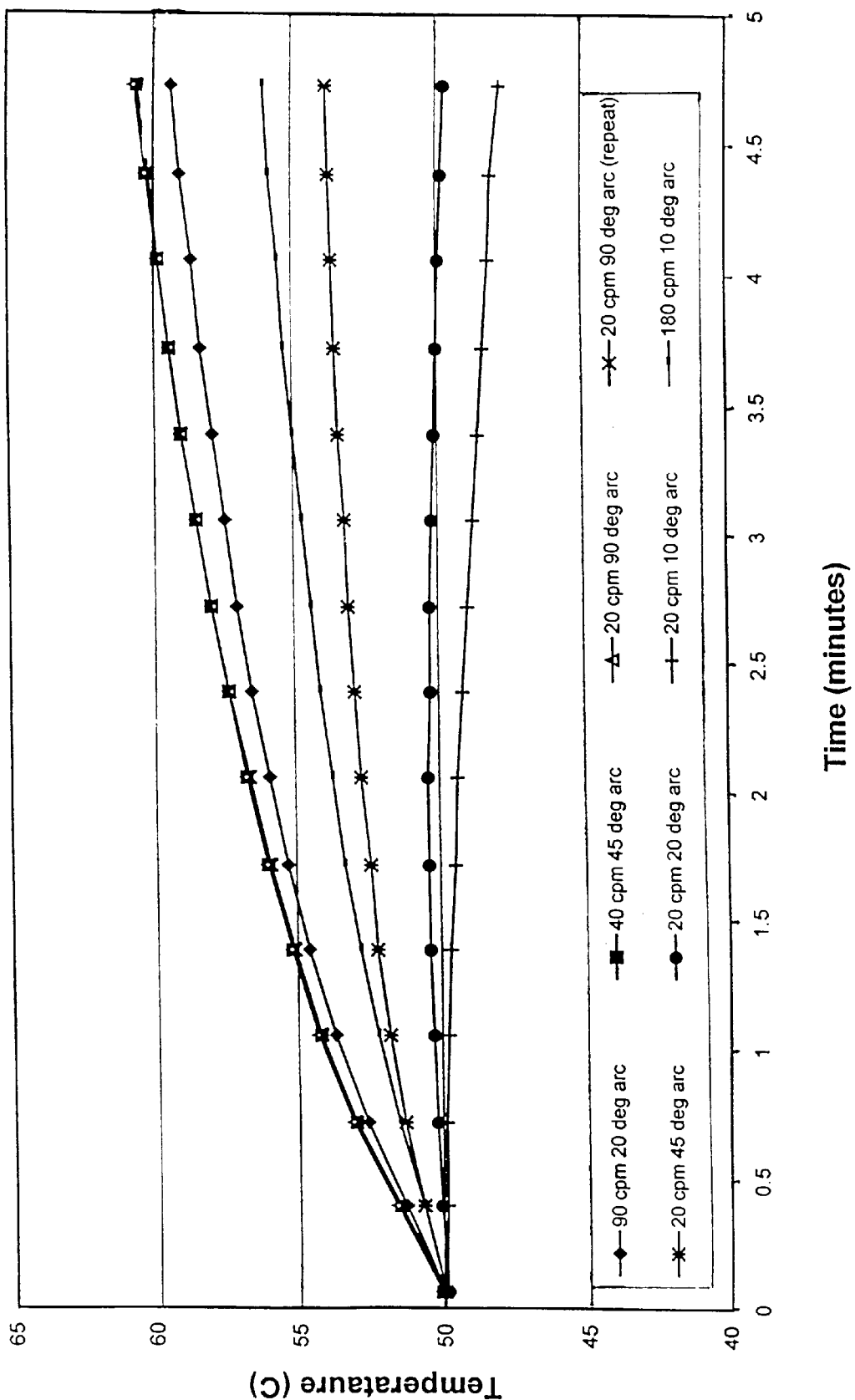
FIG. 4 is a temperature profile of an upper die plate from viscous heating of an SBR compound with 75 phr N351, wherein the die cavity is filled with an elastomeric material.

FIGS. 3 and 4 respectfully show the rise in temperature of the lower and upper plates 26, 25 for a Styrene Butadiene Rubber (SBC) Compound with 75 phr (parts per hundred rubber) of N351 carbon black when exposed to sinusoidal movement of the lower die plate 26 at different combinations of amplitudes of oscillation (strain) and frequency, with a Tstart of 50° C. With reference to the legends in FIGS. 3 and 4, the numeric value preceding "cpm" refers to the cycles per minute (frequency), while the numeric value preceding "arc" refers to the amplitude of oscillation. Therefore, test condition "90 cpm20 deg arc" refers to 90 cycles per minute at an amplitude of oscillation of +/−20° of arc.

For uncured rubber, it has been found that the combination of a frequency of 20 cycles per minute (0.33 Hz) and 90 degrees arc strain (1256% strain) give the highest level of measured viscous heating as indicated from the recorded temperatures of the upper and lower dies with very good repeatability. Moreover, it can be observed from FIGS. 3 and 4, that the temperature changes for "90 cpm20 deg arc" closely approximates the temperature changes for "180 cpm 10 deg arc." Accordingly, a correlation has been observed between: (1) the product of (a) the frequency of oscillation and (b) the amplitude of oscillation, and (2) the measured temperature changes. It has been further observed that in some cases the temperature of the sample material begins to decrease after a period of time, due to reductions in the viscosity of the sample material at higher temperatures. For example, this is observed in FIGS. 3 and 4, with regard to test condition "20 cpm 10 deg arc." The most significant data values that are obtained include the maximum temperature obtained during oscillations (Tmax) and the rate of temperature increase (Rt).

As can be observed from FIGS. 3 and 4, the temperature changes measured by the temperature probe located in lower die plate 26 is greater that the temperature changes measured by the temperature probe located in upper die plate 25. Since many viscoelastic materials (e.g., rubber) are poor thermoconductors (i.e., non-uniform heat distribution), the temperature of the sample material may vary significantly at different locations thereof. As a result, it is observed that a greater amount of viscous heat is being generated in proximity to lower die plate 26 than upper die plate 25. This difference in viscous heat can be attributed to the friction (i.e., rubbing) occurring between sealing ring 28 and lower die plate 26, as lower die plate 26 rotates relative to sealing ring 28, during oscillation. There is virtually no measurable friction between sealing ring 27 and upper die plate 25, because upper die plate 25 remains stationary. Accordingly, it is necessary to determine the viscous heat attributed to the friction, and subtract out this viscous heat from the values obtained in connection with FIG. 4.

Prior to beginning testing with a sample material in the die cavity, a preliminary "empty test" is run. In the empty test, die plates 25, 26 are moved to a closed position to form an empty die cavity. The die cavity is first heated to a temperature (Tprelim) in the range of approximately 70° to 120° C., by activating the respective heating elements. Next, the heating elements are deactivated and the die cavity is allowed to cool and stabilize to the predetermined starting temperature (Tstart). It should be appreciated that both the upper and lower die plates 25, 26 are stabilized at Tstart. Moreover, it may be necessary to regulate the respective heating elements to stabilize the temperature of the die plates. Once the temperature has stabilized (i.e., reached thermal equilibrium) at Tstart, heating elements and cooling devices are deactivated, and the lower die plate 26 is oscillated at a predetermined amplitude and a predetermined frequency. Changes in temperature are used to obtain empty-cavity heat values.

Figure 5:
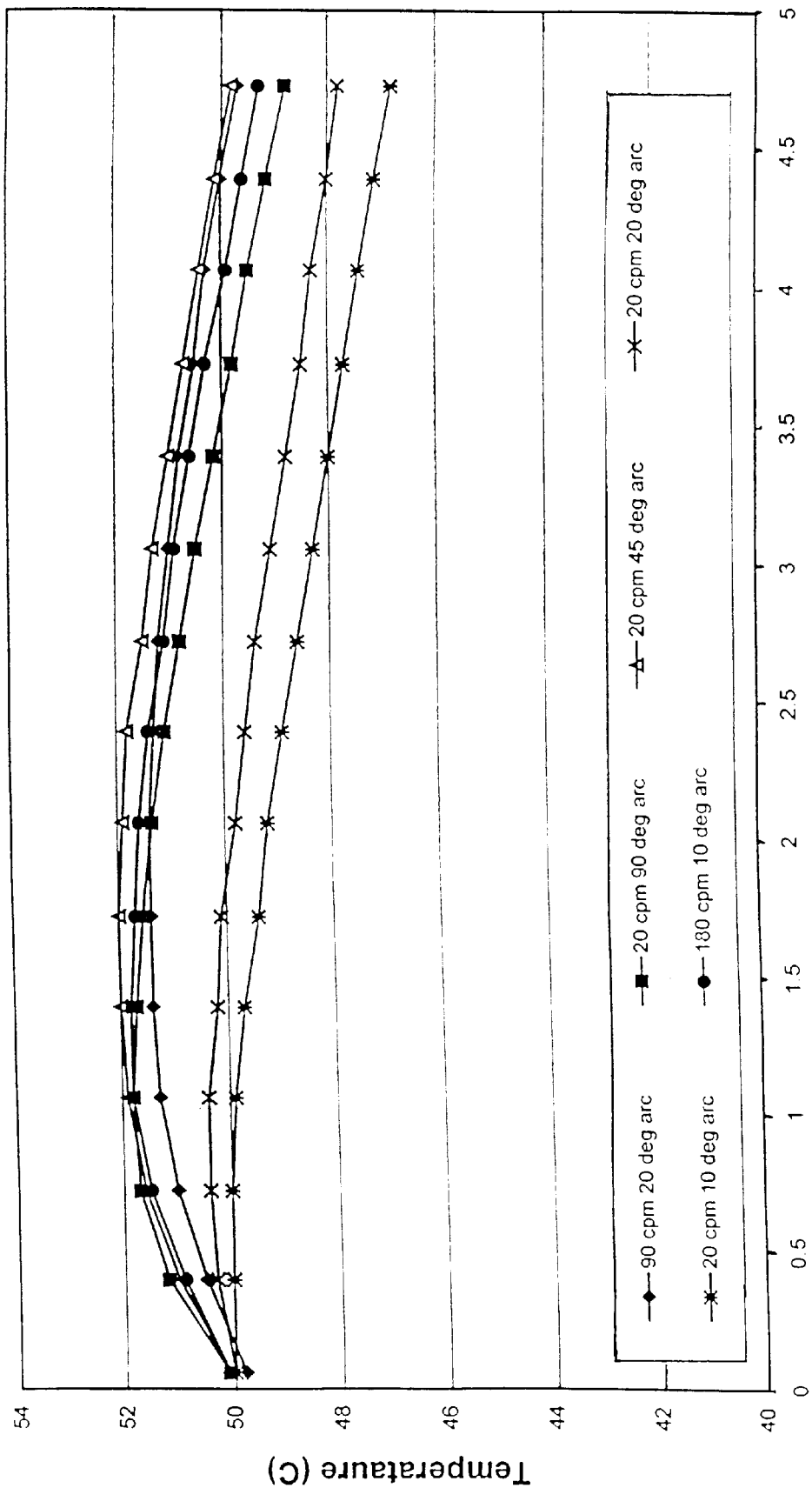
FIG. 5 is a temperature profile of a lower die plate from specified conditions of frequency and strain, wherein the die cavity is empty.
Figure 6:
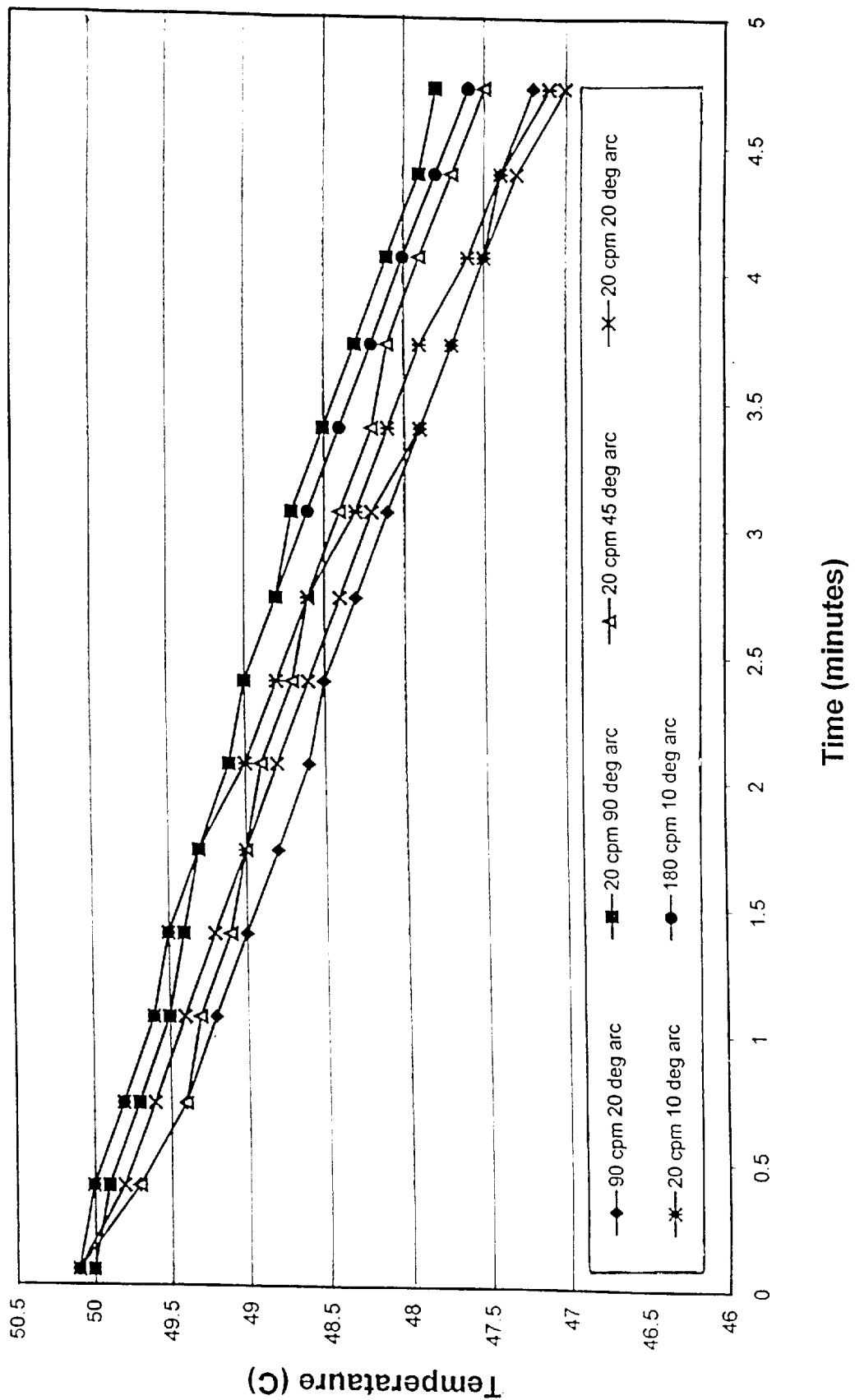
FIG. 6 is a temperature profile of an upper die plate from specified conditions of frequency and strain, wherein the die cavity is empty.

FIGS. 5 and 6 respectfully show the change in temperature of the lower and upper plates 26, 25 with an empty die cavity, when exposed to sinusoidal movement of the lower die plate 26 at different combinations of amplitudes of oscillation (strain) and frequency, with a Tstart of 50° C. As can be seen, lower die plate 26 shows a temperature rise of up to about 2 degrees C above Tstart due solely to sealing ring 28. Since upper die plate 25 does not actually move, there is no heat input from sealing ring 27, and the recorded temperatures of upper die plate 25 only drops with time.

Figure 7:
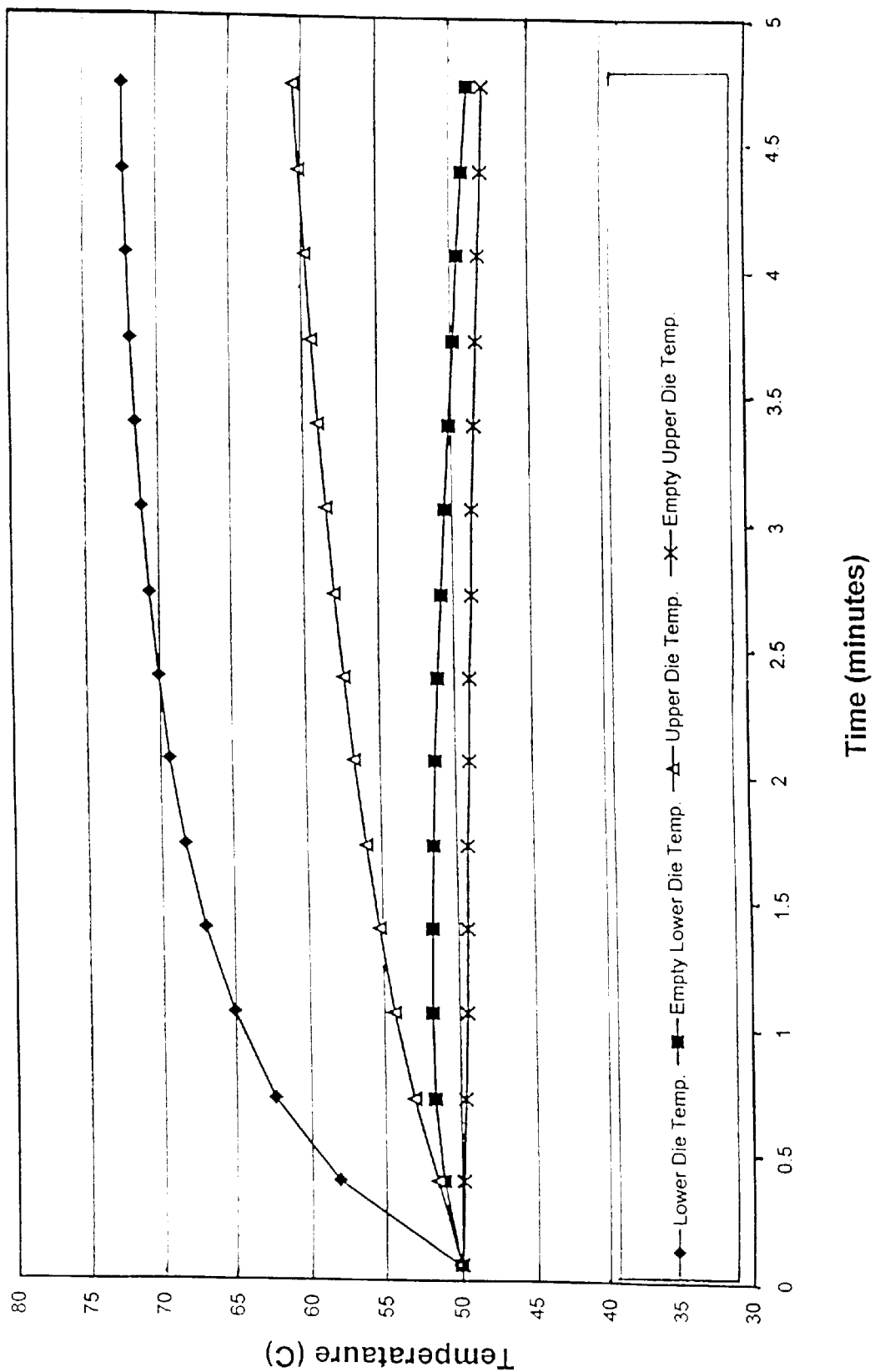
FIG. 7 provides temperature profiles for both lower and upper die plates with an SBR compound, wherein the die cavity is both empty and filled, and strain and frequency are fixed.

FIG. 7 provides temperature profiles for both lower and upper die plate, with filled and empty die cavities, at a fixed strain and frequency.

By subtracting the temperatures of the lower and upper die plates, with an empty die cavity ($t_{Le}$ and $t_{Ue}$) from the apparent temperature rise of the lower and upper die plates, with a filled die cavity ($t_{appL}$ and $t_{appU}$), the "delta temperature ($\Delta T$) is respectfully calculated as follows:

$$\Delta T_{lower} t_{appL} - t_{Le}$$

$$\Delta T_{upper} = t_{appU} - t_{Ue}$$

Figure 8:
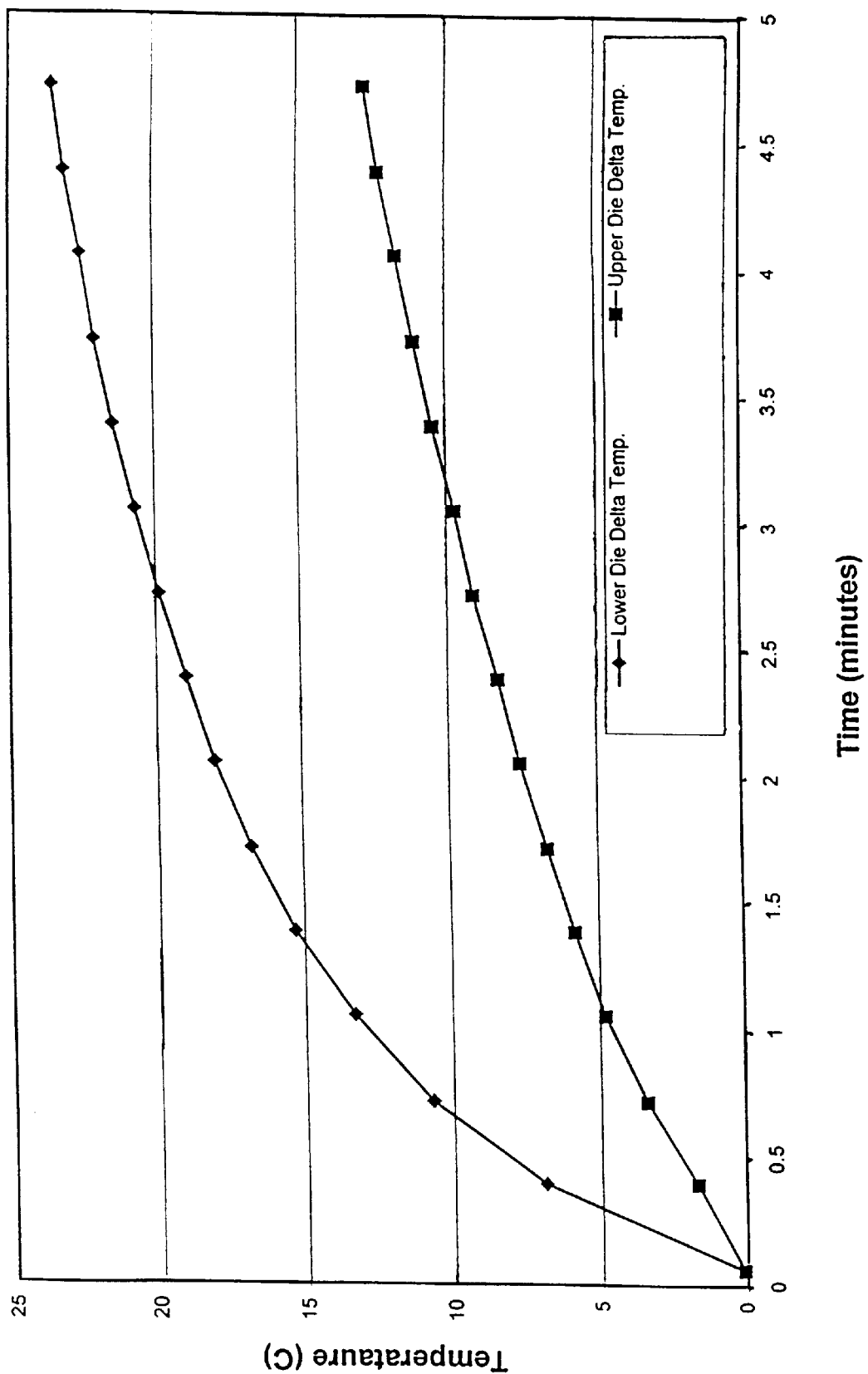
FIG. 8 shows the calculated ΔT for lower and upper die plates while testing an SBR compound with 75 phr N351.

As can be seen from FIG. 8, the calculated $\Delta T$ is significantly higher in connection with the lower die plate ($\Delta T_{Lower}$) as compared to the upper die plate ($\Delta T_{Upper}$), even after correcting for heat contribution from the lower sealing ring 28.

The test data discussed above can be utilized to measure the viscous heating effects of different admixtures (e.g., fillers and reinforcing agents). In this regard, tests can be run on various types of sample compounds that are prepared with different admixtures to determine values for viscous heating.

It should be further appreciated that while the present invention has been described in connection with measuring viscous heat of a viscoelastic material in an uncured state, the present invention is also suitable for measuring viscous heat (i.e., "heat build-up") of a viscoelastic material in a cured state. Of course, in the cured state, there is usually a limit to the level of strain that can be applied with a typical RPA. However, as seen previously from FIGS. 3 and 4 for viscous heating, increasing the frequency is almost as effective for increasing the temperature of the sample material as increasing the strain.

In the case of a cured state measurement, Tprelim is selected as a temperature greater than or equal to the cure temperature (Tcure), so that the sample material cures. Tcure is typically in the range of approximately 80° C. to 200° C. In accordance with a preferred embodiment of the present invention, Tstart is preferably selected as a temperature less than or equal Tcure. This ensures that the viscosity is not so high as to prevent the measurement of viscous heating. In this regard, if the viscosity of the sample material is too high, the capacity of the apparatus to apply a shearing force to the sample material will be exceeded. However, with the appropriate apparatus and sample material properties it may be possible to establish Tstart at a temperature above Tcure.

The significant utility of the present invention should now be recognized. In this regard, the present invention provides a single apparatus suitable for determining viscous heating/ heat build-up for a viscoelastic material in both the cured and uncured state. In fact, a simple testing procedure can be arranged so that viscous heating in the uncured state is first determined, followed by a determination of heat build-up in the cured state. For instance, uncured viscoelastic sample material is first tested to evaluate viscous heating. Immediately after completion of this evaluation, the sample material may be heated to a temperature which cures the material. Next, the sample material is cooled and tested to evaluate heat build-up.

The invention has been described with reference to a preferred embodiment. Obviously, modifications and alterations will occur to others upon a reading and understanding of this specification. It is intended that all such modifications and alterations be included insofar as they come within the scope of the appended claims or the equivalents thereof.

Having thus described the invention, it is now claimed:

1. A method for measuring viscous heating of a viscoelastic material, comprising:
   applying a predetermined pressure to the viscoelastic material;
   regulating heating means to bring the viscoelastic material to a first predetermined temperature;
   deactivating said heating means;
   applying a shearing force to the viscoelastic material;
   measuring the change in temperature of the viscoelastic material during application of the shearing force, to obtain heat values.

2. A method according to claim 1, wherein said step of applying a predetermined pressure to the viscoelastic material includes compressing the viscoelastic material between a stationary die plate and a rotatable die plate.

3. A method according to claim 2, wherein said step of applying a shearing force to the viscoelastic material includes oscillating said rotatable die plate with a predetermined amplitude and a predetermined frequency.

4. A method according to claim 1, wherein said step of applying a predetermined pressure to the viscoelastic material includes moving (1) a first die assembly including a stationary die plate, and (2) a second die assembly including a rotatable die plate, to a closed position to form a die cavity.

5. A method according to claim 1, wherein said first predetermined temperature is below the cure temperature of the viscoelastic material.

6. A method according to claim 5, wherein said first predetermined temperature is in the range of approximately 20° C. to 120° C.

7. A method according to claim 1, wherein said first predetermined temperature is a temperature equal to or greater than the cure temperature of the viscoelastic material.

8. A method according to claim 1, wherein said viscoelastic material is cured prior to application of the shearing force to the viscoelastic material.

9. A method according to claim 1, wherein said step of regulating said heating means includes:

heating the viscoelastic material to a second predetermined temperature exceeding said first predetermined temperature; and cooling the viscoelastic material to said first predetermined temperature.

10. A method according to claim 1, wherein prior to said step of applying a predetermined pressure to the viscoelastic material:

moving first and second die plates to a closed position to form a die cavity, wherein said die cavity is empty and one of said die plates is rotatable relative to the other die plate;

regulating said heating means to bring said die cavity to said first predetermined temperature;

rotating said rotatable die plate;

measuring the change in temperature at the rotatable die plate in response to rotation thereof, to obtain empty-cavity heat values.

11. A method according to claim 10, wherein said empty-cavity heat values are subtracted from said heat values to obtain viscous heat values.

12. A method according to claim 10, wherein said step of rotating said rotatable die plate includes oscillating said rotatable die plate with a predetermined amplitude and a predetermined frequency.

13. An apparatus for measuring viscous heating of a viscoelastic material, comprising:

means for applying a predetermined pressure to the viscoelastic material;

heating means for heating the viscoelastic material;

control means for regulating the heating means to bring the viscoelastic material to a first predetermined temperature and to deactivate said heating means once said first predetermined temperature is reached;

means for applying a shearing force to the viscoelastic material;

means for measuring the change in temperature of the viscoelastic material during application of the shearing force, to obtain heat values.

14. An apparatus according to claim 13, wherein said means for applying a predetermined pressure to the viscoelastic material includes a stationary die plate and a rotatable die plate.

15. An apparatus according to claim 14, wherein said means for applying a shearing force to the viscoelastic material includes means for oscillating said rotatable die plate with a predetermined amplitude and a predetermined frequency.

16. An apparatus according to claim 13, wherein said means for applying a predetermined pressure to the viscoelastic material includes:

a first die assembly including a stationary die plate, and a second die assembly including a rotatable die plate, wherein said first and second die assembly are movable to a closed position to form a die cavity.

17. A method for measuring viscous heating of a viscoelastic material, comprising:

regulating heating means to bring the viscoelastic material to a first predetermined temperature;

deactivating said heating means;

applying a strain to the viscoelastic material;

measuring the change in temperature of the viscoelastic material during application of the strain, to obtain heat values.

18. A method according to claim 17, wherein said step of applying a shearing force to the viscoelastic material includes rotating a second die plate relative to a first die plate, with a predetermined amplitude and a predetermined frequency.

19. A method according to claim 17, wherein said viscoelastic material is in an uncured state when applying the strain to said viscoelastic material.

20. A method according to claim 17, wherein said viscoelastic material is in a cured state when applying the strain to said viscoelastic material.

* * * * *